(12) United States Patent
Yoshikawa et al.

(10) Patent No.: US 9,079,819 B2
(45) Date of Patent: Jul. 14, 2015

(54) METHOD FOR PRODUCING CIS-1,3,3,3-TETRAFLUOROPROPENE

(71) Applicant: Central Glass Company, Limited, Ube-shi, Yamaguchi (JP)

(72) Inventors: Satoshi Yoshikawa, Saitama (JP); Satoru Okamoto, Kawagoe (JP); Yoshio Nishiguchi, Kawagoe (JP); Fuyuhiko Sakyu, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 14/394,219

(22) PCT Filed: Apr. 2, 2013

(86) PCT No.: PCT/JP2013/060044
§ 371 (c)(1),
(2) Date: Oct. 13, 2014

(87) PCT Pub. No.: WO2013/157384
PCT Pub. Date: Oct. 24, 2013

(65) Prior Publication Data
US 2015/0080618 A1 Mar. 19, 2015

(30) Foreign Application Priority Data

Apr. 16, 2012 (JP) .................. 2012-092683

(51) Int. Cl.
C07C 17/25 (2006.01)
C07C 17/23 (2006.01)
C07C 17/383 (2006.01)

(52) U.S. Cl.
CPC ............. *C07C 17/23* (2013.01); *C07C 17/25* (2013.01); *C07C 17/383* (2013.01)

(58) Field of Classification Search
CPC ........................................................ C07C 17/25
USPC ........................................................ 570/156
See application file for complete search history.

(56) References Cited

U.S. PATENT DOCUMENTS 2,480,560 A   8/1949   Downing
6,124,510 A   9/2000   Elsheikh et al.
7,485,760 B2   2/2009   Wang et al.
7,638,660 B2   12/2009   Wang et al.
2008/0051610 A1   2/2008   Wang et al.
2009/0118555 A1   5/2009   Wang et al.
2012/0046505 A1   2/2012   Nappa et al.
2012/0065435 A1   3/2012   Nishiguchi et al.

FOREIGN PATENT DOCUMENTS

| JP | 9-67281 A | 3/1997 |
| JP | 10-17502 A | 1/1998 |
| JP | 11-140002 A | 5/1999 |
| JP | 2000-7591 A | 1/2000 |
| JP | 2000-7592 A | 1/2000 |
| JP | 2000-63300 A | 2/2000 |
| JP | 2000-143561 A | 5/2000 |
| JP | 2008-19243 A | 1/2008 |
| JP | 2008-69147 A | 3/2008 |
| WO | WO 2010/129844 A1 | 11/2010 |
| WO | WO 2012/035851 A1 | 3/2012 |

OTHER PUBLICATIONS

Haszeldine et al., "Part II. Radical Addition to Olefins of the Type R—CH—CH2," Addition of Free Radicals to Unsaturated Systems, J. Chem. Soc., 1953, pp. 1199-1206, Cambridge University, Cambridge, UK.
Knunyants et al., "Communication 13. Catalytic Hydrogenation of Perfluoro Olefins," Reactions of Fluoro Olefins, Aug. 1960, Institute of Heteroorganic Compounds, Academy of Sciences of the USSR Translated from Izvestiya Akademii Nauk SSSR, No. 8, pp. 1412-1418 with English translation.
International Search Report (PCT/ISA/210) dated Jun. 18, 2013 with English translation (Five (5) pages).

*Primary Examiner* — Elvis O Price
(74) *Attorney, Agent, or Firm* — Crowell & Moring LLP

(57) ABSTRACT

A production method of cis-1,3,3,3-tetrafluoropropene according to the present invention includes the steps of: subjecting 1,1,1,3,3-pentafluoropropane to dehydrofluorination to form a reaction mixture (A) containing cis-1,3,3,3-tetrafluoropropene, trans-1,3,3,3-tetrafluoropropene and unreacted 1,1,1,3,3-pentafluoropropane; distilling the reaction mixture (A) to separate the trans-1,3,3,3-tetrafluoropropene from the reaction mixture (A) and collect a reaction mixture (B) containing the cis-1,3,3,3-tetrafluoropropene and the 1,1,1,3,3-pentafluoropropane; and reacting the reaction mixture (B) with a base and thereby obtaining the cis-1,3,3,3-tetrafluoropropene from the reaction mixture (B). This production method enables efficient production of high-purity cis-1,3,3,3-tetrafluoropropene and thus has industrial advantages.

11 Claims, No Drawings

METHOD FOR PRODUCING CIS-1,3,3,3-TETRAFLUOROPROPENE

FIELD OF THE INVENTION

The present invention relates to a method for producing cis-1,3,3,3-tetrafluoropropene.

BACKGROUND ART

As methods for production of 1,3,3,3-tetrafluoropropene, there are conventionally known a method of dehydroiodonating 1,3,3,3-tetrafluoro-1-iodopropane with alcoholic potassium hydroxide (see Non-Patent Document 1) and a method of dehydrofluorinating 1,1,1,3,3-pentafluoropropane (HFC-245fa) with potassium hydroxide in dibutyl ether (see Non-Patent Document 2). Further, Patent Document 1 discloses a method of dehydrofluorinating 1,1,1,3,3-pentafluoropropane with a chromium/activated carbon catalyst. Patent Document 2 discloses a method for producing 1,3,3,3-tetrafluoropropene by contact of 1,1,1,3,3-pentafluoropropane with a chromium-based catalyst.

On the other hand, there are disclosed, as examples of gas-phase dehydrofluorination reaction of ordinary fluoroalkane, a method of converting gaseous 1,1,1,3,3,3-hexafluoropropane to a corresponding propene by contact with an activated carbon or chromium oxide catalyst as in Patent Document 3 and a method of thermally decomposing fluoroethane by contact with an activated carbon as in Patent Document 4.

Furthermore, Patent Document 5 discloses a method for producing 1,3,3,3-tetrafluoropropene by dehydrofluorinating 1,1,1,3,3-pentafluoropropane in a gas phase in the presence of a zirconium compound-carrying catalyst that carries a zirconium compound on a metal oxide or activated carbon.

PRIOR ART DOCUMENTS

Patent Documents

Patent Document 1: Japanese Laid-Open Patent Publication No. H11-140002
Patent Document 2: Japanese Laid-Open Patent Publication No. 2000-63300
Patent Document 3: Japanese Laid-Open Patent Publication No. H09-67281
Patent Document 4: U.S. Pat. No. 2,480,560
Patent Document 5: Japanese Laid-Open Patent Publication No. 2008-019243

Non-Patent Documents

Non-Patent Document 1: R. N. Haszeldine et al., J. Chem. Soc., 1953, 1199-1206; CA 48 5787f
Non-Patent Document 2: I. L. Knunyants et al., Izvest. Akad. Nauk S. S. S. R., Otdel. Khim. Nauk., 1960, 1412-1418; CA 55 349f

SUMMARY OF THE INVENTION

Problems to be Solved by the Invention

The methods of Non-Patent Documents 1-2, each of which involves dehydrohalogenation reaction with potassium hydroxide, are high in reaction rate and selectivity. However, there are many difficulties in industrial applications of these methods due to the facts that: the reaction needs to be performed in a solvent; the potassium hydroxide needs to be used in a stoichiometric amount or more; and there occurs a great amount of potassium salt as a result of the reaction.

The gas-phase dehydrofluorination reaction of fluoroalkane is generally not so high in conversion rate even under severe reaction conditions. For example, the method of Patent Document 3, which involves dehydrofluorination reaction of gaseous 1,1,1,3,3,3-hexafluoropropane with an activated carbon or chromium oxide catalyst, shows approximately quantitative selectivity but results in a conversion rate of the order 4 to 50%.

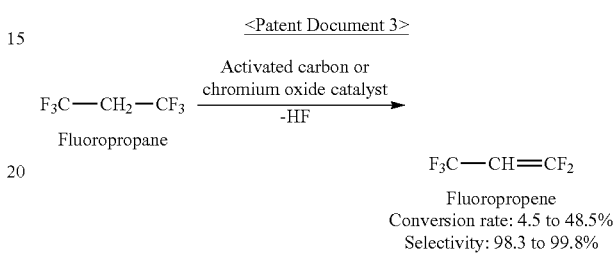

The method of Patent Document 4, which involves thermal composition at a considerably high temperature of about 750 to 900° C., results in a conversion rate of the order of 40%.

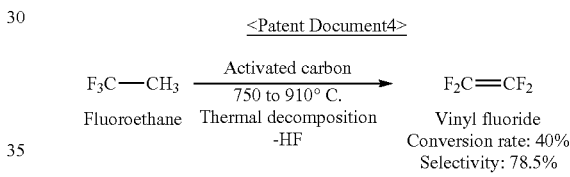

The above dehydrofluorination reaction needs to be performed under more severe reaction conditions for improvement in conversion rate. It is however assumed that the severe reaction conditions, including high reaction temperature, makes it difficult to apply the dehydrofluorination reaction for industrial production purposes in view of conversion of the reaction product to tar, carbonization of the reaction product, durability of the reactor and the like.

The target compound of the present invention, i.e., 1,3,3,3-tetrafluoropropene has a double bond in its molecule and can exist as "trans" and "cis" structural isomers. Against the foregoing backdrop, it is often the case that 1,3,3,3-tetrafluoropropene is obtained in the form of a mixture of these isomers when produced by any of the methods disclosed in the prior art (see, for example, Patent Document 5). The prior art does not clearly disclose a "selective production method" suitable for industrial scale production of cis-1,3,3,3-tetrafluoropropene as the target compound of the present invention.

It is accordingly an object of the present invention to provide a method for producing target cis-1,3,3,3-tetrafluoropropene with a high conversion rate and high efficiency on an industrial scale.

Means for Solving the Problems

The present inventors have made extensive researches to solve the above problems and, as a results, found various means for allowing dehydrofluorination of 1,1,1,3,3-pentafluoropropane to proceed with a high conversion rate and separating and purifying cis-1,3,3,3-tetrafluoropropene with a high yield from the resulting reaction mixture of trans and cis isomers. The present invention is based on these findings.

Namely, the present invention provides a method for production of 1,3,3,3-tetrafluoropropene as defined in the following inventive aspects 1-12.

[Inventive Aspect 1]

A method for production of cis-1,3,3,3-tetrafluoropropene, comprising:
- a first step of subjecting 1,1,1,3,3-pentafluoropropane to dehydrofluorination to form a reaction mixture containing cis-1,3,3,3-tetrafluoropropene, trans-1,3,3,3-tetrafluoropropene and unreacted 1,1,1,3,3-pentafluoropropane;
- a second step of distilling the reaction mixture formed by the first step to separate the trans-1,3,3,3-tetrafluoropropene from the reaction mixture and collect a reaction mixture containing the cis-1,3,3,3-tetrafluoropropene and 1,1,1,3,3-pentafluoropropane; and
- a third step of reacting the reaction mixture collected by the second step and containing the cis-1,3,3,3-tetrafluoropropene and 1,1,1,3,3-pentafluoropropane with a base and thereby obtaining the cis-1,3,3,3-tetrafluoropropene from the reaction mixture.

[Inventive Aspect 2]

The method according to Inventive Aspect 1, wherein, in the first step, the dehydrofluorination is performed in a gas phase in the presence of a catalyst.

[Inventive Aspect 3]

The method according to Inventive Aspect 2, wherein the catalyst is a zirconium compound-carrying catalyst that carries a zirconium compound on a metal oxide or activated carbon.

[Inventive Aspect 4]

The method according to Inventive Aspect 3, wherein the metal oxide is at least one kind selected from the group consisting of alumina, zirconia, titania and magnesia.

[Inventive Aspect 5]

The method according to Inventive Aspect 3 or 4, wherein the zirconium compound is in the form of at least one kind selected from the group consisting of a nitrate, a phosphate, a fluoride, a chloride, a fluorochloride, an oxyfluoride, an oxychloride and an oxyfluorochloride.

[Inventive Aspect 6]

The method according to any one of Inventive Aspects 1 to 5, wherein the first step or the second step includes removing hydrogen fluoride from the reaction mixture.

[Inventive Aspect 7]

The method according to any one of Inventive Aspects 1 to 6, further comprising: a step of converting the trans-1,3,3,3-tetrafluoropropene separated by the distillation of the second step to 1,1,1,3,3-pentafluoropropane, and then, recycling the 1,1,1,3,3-pentafluoropropane as the raw material of the first step.

[Inventive Aspect 8]

The method according to Inventive Aspect 7, wherein the conversion of the trans-1,3,3,3-tetrafluoropropene is performed by reaction with hydrogen fluoride in a gas phase in the presence of a catalyst.

[Inventive Aspect 9]

The method according to any one of Inventive Aspects 1 to 8, wherein the base used in the third step is a hydroxide of an alkali metal or a hydroxide of an alkaline earth metal.

[Inventive Aspect 10]

The method according to Inventive Aspect 9, wherein the alkali metal is lithium, sodium, potassium, rubidium or cesium; and wherein the alkaline earth metal is magnesium, calcium or strontium.

[Inventive Aspect 11]

A method for simultaneous production of cis-1,3,3,3-tetrafluoropropene and trans-1,3,3,3-tetrafluoropropene, comprising:
- a first step of subjecting 1,1,1,3,3-pentafluoropropane to dehydrofluorination so form a reaction mixture containing cis-1,3,3,3-tetrafluoropropene, trans-1,3,3,3-tetrafluoropropene and unreacted 1,1,1,3,3-pentafluoropropane;
- a second step of distilling the reaction mixture formed by the first step to separate the trans-1,3,3,3-tetrafluoropropene from the reaction mixture and collect a reaction mixture containing the cis-1,3,3,3-tetrafluoropropene and 1,1,1,3,3-pentafluoropropane; and
- a third step of reacting the reaction mixture collected by the second step and containing the cis-1,3,3,3-tetrafluoropropene and 1,1,1,3,3-pentafluoropropane with a base and thereby obtaining the cis-1,3,3,3-tetrafluoropropene from the reaction mixture.

[Inventive Aspect 12]

A method for production of high-purity cis-1,3,3,3-tetrafluoropropene, comprising: purifying the cis-1,3,3,3-tetrafluoropropene obtained by the method according to any one of Inventive Aspects 1 to 11.

The target compound of the present invention, i.e., 1,3,3,3-tetrafluoropropene can exist as cis and trans structural isomers and thus can be obtained in the form of a reaction mixture of these isomers. Further, the reaction mixture often contains other components such as 1,1,1,3,3-pentafluoropropane and hydrogen fluoride. It has been very difficult to separate cis-1,3,3,3-tetrafluoropropene and 1,1,1,3,3-pentafluoropropane from each other by distillation because cis-1,3,3,3-tetrafluoropropene and 1,1,1,3,3-pentafluoropropane form an azeotropic-like composition.

Although the dehydrofluorination of 1,1,1,3,3-pentafluoropropane is conventionally widely known, the principle purpose of the use of this reaction has been to produce trans-1,3,3,3-tetrafluoripropene with a high yield.

By contrast, the production method of the present invention enables production of high-purity cis-1,3,3,3-tetrafluoropropene by the above-mentioned steps. The production method of the present invention is thus easily applicable and useful for industrial scale production. It is therefore possible to produce target cis-1,3,3,3-tetrafluoropropene with high productivity and without environmental load.

The production method of the present invention provides the effects that cis-1,3,3,3-tetrafluoropropene can be obtained with a high yield by using industrially available 1,1,3,3,3-pentafluoropropane as the raw material and performing the respective steps favorably under suitable reaction conditions.

DESCRIPTION OF THE EMBODIMENTS

Hereinafter, the present invention will be described in detail below.

[First Step]

The first step will be first explained below. In the first step, 1,1,1,3,3-pentafluoropropane is subjected to dehydrofluorination so as to form a reaction mixture containing cis-1,3,3,3-tetrafluoropropene, trans-1,3,3,3-tetrafluoropropene and unreacted 1,1,1,3,3-pentafluoropropane.

The 1,1,1,3,3-pentafluoropropane used as the raw material of the present invention is industrially produced and readily available as a blowing agent for rigid polyurethane foams etc. It is feasible to prepare the 1,1,1,3,3-pentafluoropropane by any conventionally known process as disclosed in Japanese Laid-Open Patent Publication No. 2000-007591, Japanese Laid-Open Patent Publication No. 2000-007592, Japanese Laid-Open Patent Publication No. 2000-143561 etc.

In the first step, the dehydrofluorination of the 1,1,1,3,3-pentafluoropropane can be performed in a liquid phase or in a gas phase.

In the case of the gas phase, the dehydrofluorination is preferably performed in the presence of a catalyst. As the catalyst, preferred is a zirconium compound-carrying catalyst that carries a zirconium compound on a metal oxide or activated carbon.

A zirconium catalyst, such as the zirconium compound-carrying catalyst carrying the zirconium compound on the metal oxide or activated carbon or zirconia, is suitably usable in the first step.

The zirconium compound suitably used for preparation of the zirconium compound-carrying catalyst is at least one kind selected from the group consisting of a nitrate, a phosphate, an oxide, a fluoride, a chloride, a fluorochloride, an oxyfluoride, an oxychloride and an oxyfluorochloride of zirconium.

The metal oxide usable as the catalyst carrier is at least one kind selected from the group consisting of alumina, zirconia, titania and magnesia. The activated carbon usable as the catalyst carrier is any of various kinds of commercially available activated carbons. Example of such commercially available activated carbons are bituminous coal activated carbons (such as "Calgon Granular Activated Carbon CAL" manufactured by Toyo Calgon Co., Ltd.) and coconut shell activated carbons (such as "Granular SHIRASAGI G series" manufactured by Japan Enviro Chemicals Ltd.). As a matter of course, the activated carbon is not limited to those of the above kinds and manufacturers.

There is no particular limitation on the process for preparation of the zirconium compound-carrying catalyst. It is feasible to prepare the zirconium compound-carrying catalyst by providing a solution of a soluble zirconium compound, and then, impregnating the carrier with the provided solution or spraying the provided solution onto the carrier. The carrier such as metal oxide or activated carbon may be subjected in advance to halogen modification treatment with hydrogen fluoride, hydrogen chloride, chlorofluorinated hydrocarbon etc.

The amount of the zirconium compound carried is generally 0.1 to 80 wt %, preferably 1 to 40 wt %, based on the total weight of the zirconium compound and the carrier. As the soluble zirconium compound carried on the carrier, there can be used those soluble in solvents such as water, hydrochloric acid, ammonia water, ethanol and acetone. Examples of such soluble zirconium compounds are nitrate, phosphate, chloride, oxide, oxychloride and oxyfluoride of zirconium.

A compound of at least one kind of metal selected from the group consisting of chromium, titanium, aluminum, manganese, nickel, cobalt, iron, molybdenum, niobium, tantalum, iridium, tin, hafnium and vanadium may be additionally carried so as to allow coexistence of zirconium with the additional metal.

Regardless of how the metal-carrying catalyst is prepared, it is effective to treat the catalyst with a fluorination agent such as hydrogen fluoride or fluorinated hydrocarbon at a temperature higher than a predetermined reaction temperature in advance of use for the purpose of activation of the catalyst. It is also effective to feed oxygen, chlorine, fluorinated or chlorinated hydrocarbon or the like into the reactor during the reaction for the purpose of improvements in catalyst life, reaction rate and reaction yield.

The reaction temperature is generally 200 to 600° C., preferably 200 to 500° C., more preferably 200 to 400° C. If the reaction temperature is lower than 200° C., the reaction is slow and is not always said to be practical. If the reaction temperature exceeds 600° C., the lifetime of the catalyst is shortened. In addition, the reaction proceeds rapidly but causes deterioration in the selectivity of the 1,3,3,3-tetrafluoropropene by generation of decomposition products at such a high reaction temperature. It is a particularly preferred embodiment of the present invention to control the reaction temperature to within the range of 300 to 350° C. due to the fact that the generation of by-products can be significantly inhibited within such a temperature range.

In the first step, the 1,1,1,3,3-pentafluoropropane can be supplied together with an inert gas such as nitrogen, helium or argon into the reaction system. Hydrogen fluoride may coexist in the 1,1,1,3,3-pentafluoropropane.

There is no particular limitation on the reaction pressure. In view of equipment durability, the reaction pressure is preferably 0.1 to 10 kg/cm$^2$. It is preferable to select the pressure conditions that does not cause liquefaction of the organic raw material and hydrogen fluoride in the reaction system. The contact time is generally 0.1 to 300 seconds, preferably 5 to 200 seconds.

The reactor used in the first step can be formed of a material having not only heat resistance but also resistance to corrosion by hydrogen fluoride or hydrogen chloride etc. Among others, stainless steel, Hastelloy alloy, Monel alloy or platinum is preferred as the material of the reactor. The reactor may alternatively be formed of a material having a lining of the above metal.

The thus-obtained 1,3,3,3-tetrafloropropene product flowing out of the reactor in the first step is in the form of the reaction mixture containing the cis- and trans-1,3,3,3-tetrafluoropropene and unreacted 1,1,1,3,3-pentafluoropropane. Although the reaction mixture further contains acidic gas (such as hydrogen fluoride), it is feasible to remove the acid gas in the present first step or in the subsequent second step. The conditions for removal of the acid gas in the first step may be the same as those in the second step as will be explained later.

In the present invention, the target cis-1,3,3,3-tetrafluoropropene is efficiently isolated and purified from the reaction product by the following second and third steps.

The trans-1,3,3,3-tetrafluoropropene, which is formed simultaneously with the cis-1,3,3,3-tetrafluoropropene, is also separated by the following second step.

[Second Step]

The second step will be next explained below. In the second step, the reaction mixture formed by the first step is subjected to distillation so as to separate the trans-1,3,3,3-tetrafluoropropene from the reaction mixture and collect a reaction mixture containing the cis-1,3,3,3-tetrafluoropropene and the 1,1,1,3,3-pentafluoropropane.

As hydrogen fluoride is contained in the reaction mixture formed by the first step, it is necessary to remove the hydrogen fluoride from the reaction mixture.

There is no particular limitation on the operation for removal of hydrogen fluoride. The removal of the hydrogen fluoride may be performed on the reaction mixture immediately before the distillation or may be performed on the respective fractions of the distillation. Alternatively, the removal of the hydrogen fluoride may be performed in the above-mentioned first step (see the after-mentioned working examples). The timing of the removal of the hydrogen fluoride is adjusted as appropriate by those skilled in the art. (In the case where the removal of the hydrogen fluoride is performed in the first step, the removal of the hydrogen fluoride is not specifically required and can be optionally performed in the second step.)

There is also no particular limitation on the process for removal of hydrogen fluoride. It is feasible to remove the hydrogen fluoride by contact treatment with sulfuric acid, by washing with water or the like. For example, the hydrogen fluoride can be removed sufficiently by blowing the reaction mixture formed by the first step into water.

It is alternatively feasible to separate the hydrogen fluoride as a complex of the hydrogen fluoride with potassium fluoride, sodium fluoride or the like. For example, the hydrogen fluoride can be separated from the reaction mixture by reacting the hydrogen fluoride with a calcium salt such as calcium chloride, calcium hydroxide, calcium oxide or calcium carbonate or an aqueous solution thereof and immobilizing the hydrogen fluoride as calcium fluoride ($CaF_2$).

The hydrogen fluoride can be removed from the reaction mixture by reacting the hydrogen fluoride with an alkali metal salt such as sodium chloride or potassium chloride and immobilizing the hydrogen fluoride as a corresponding metal fluoride salt.

In the case of using sulfuric acid, it is feasible to remove and recover the hydrogen fluoride by separating the reaction mixture into a liquid phase mainly composed of the hydrogen fluoride and sulfuric acid and a gas phase mainly composed of the organic substance such as 1,3,3,3-tetrafluoropropene (cis and trans isomers) and 1,1,1,3,3-pentafluoropropane, and then, separating the hydrogen fluoride from the liquid phase.

The amount of the sulfuric acid used is varied depending on the amount of the hydrogen fluoride contained in the reaction mixture and is adjusted as appropriate by those skilled in the art. The minimum required amount of the sulfuric acid can be determined based on the solubility of hydrogen fluoride in 100% sulfuric acid with reference to a solubility-temperature graph. (For example, about 34 g of hydrogen fluoride is dissolved in 100 g of 100% sulfuric acid at 30° C.).

There is no particular limitation on the purity of the sulfuric acid used. The purity of the sulfuric acid is preferably 50% or higher, more preferably about 98 to 100%. In general, commercially available industrial sulfuric acid (purity: 98%) can be used.

The removal of the hydrogen fluoride can be performed by the use of any equipment and operation procedure that allows absorption of the hydrogen fluoride into the sulfuric acid. One conceivable operation procedure for removal of the hydrogen fluoride is to fill a bath with the sulfuric acid and blow the reaction mixture in gaseous form into the sulfuric acid within the bath. Another conceivable operation procedure for removal of the hydrogen fluoride is to blow the reaction mixture in gaseous form into a sulfuric acid scrubber packed with a packing material and cause counterflow contact of the gaseous reaction mixture with the sulfuric acid. The operation procedure is not however limited to these examples. There can be used any other operation procedure that allows absorption of the hydrogen fluoride into the sulfuric acid.

In the case of removing the hydrogen fluoride by treatment with the sulfuric acid, the removed hydrogen fluoride can be recovered and recycled. In other words, the removed hydrogen fluoride can be used as a starting material of another reaction. The sulfuric acid can be recycled for the removal of the hydrogen fluoride. For example, the hydrogen fluoride can be used as a reagent for converting the trans-1,3,3,3-tetrafluoropropene, which is formed simultaneously with the cis-1,3,3,3-tetrafluoropropene in the present invention, to 1,1,1,3,3-pentafluoropropane (the details will be described later).

After the removal of the hydrogen fluoride from the reaction mixture, the cis- and trans isomers of 1,3,3,3-tetrafluoropropene are separated from each other by the distillation of the reaction mixture. The distillation can be performed in a batch process or in a continuous process. Further, the distillation can be performed under any pressure conditions such as ordinary pressure (atmospheric pressure) or pressurized conditions. It is preferable to select the pressure conditions that can raise the condensation temperature during the distillation.

By way of example, the following explanation will be given of the case of performing the distillation by the use of a two-stage distillation system equipped with first and second distillation columns. It is needless to say that the distillation can alternatively be performed by the use of a three- or more-stage distillation system or batch distillation system.

In this case, the trans-1,3,3,3-tetrafluoropropene of low boiling point is separated and collected as a distillate from the top of the first distillation column; and the target cis-1,3,3,3-tetrafluoropropene of high boiling point is separated and collected as a distillate from the top of the second distillation column. As the cis-1,3,3,3-tetrafluoropropene (boiling point: 9° C. at room temperature and atmospheric pressure) and the 1,1,1,3,3-pentafluoropropane (boiling point: 15.3° C. at room temperature and atmospheric pressure) form an azeotropic-like composition, it is often the case that the cis-1,3,3,3-tetrafluoropropene cannot be separated from the 1,1,1,3,3-pentafluoropropane by the distillation. Thus, the cis-1,3,3,3-tetrafluoropropene is isolated efficiently by the subsequent third step.

There is no particular limitation on the distillation column as long as the distillation column has a wall surface inert to the substance under distillation. The distillation column can be formed with a wall surface of glass or stainless steel or can be formed of a base material such as steel with an inner lining of tetrafluoroethylene resin, chlorotrifluoroethylene resin, vinylidene fluoride resin, PFA resin or glass. Further, the distillation column can be a tray-type distillation column or a packed distillation column packed with a packing material such as Raschig ring, Lessing ring, Dixon ring, Pall ring, interlock saddle or Sulzer packing.

Although the distillation can be performed at ordinary pressure, it is preferable to perform the distillation under pressurized conditions in order to reduce a loss of pressure in the distillation column and decrease a load on the condenser. There is no particular limitation on the number of stages of the distillation column required for the distillation. The number of stages of the distillation column is preferably 5 to 100, more preferably 10 to 50.

[Third Step]

Next, the third step will be explained below. In the third step, the reaction mixture collected by the second step, which contains the cis-1,3,3,3-tetrafluoropropene and 1,1,1,3,3-pentafluoropropane, is reacted with a base to thereby obtain the cis-1,3,3,3-tetrafluoropropene from the reaction mixture.

The 1,1,1,3,3-pentafluoropropane contained in the reaction mixture is decomposed by reaction with the base. As a result, it is possible to obtain the cis-1,3,3,3-tetrafluoropropene with substantially no 1,1,1,3,3-pentafluoropropene.

It is herein noted that the "cis-1,3,3,3-tetrafluoropropene with substantially no 1,1,1,3,3-pentafluoropropene" refers to cis-1,3,3,3-tetrafluoropropene in which the mol ratio of 1,1,1,3,3-pentafluoropropane to cis-1,3,3,3-tetrafluoropropene is made smaller after the reaction with the base than before the reaction with the base. The mol ratio of the 1,1,1,3,3-pentafluoropropane to the cis-1,3,3,3-tetrafluoropropene is generally 1/100 or lower, preferably 1/500 or lower, more preferably 1/1000 or lower.

It is a particularly embodiment of the present invention to obtain the cis-1,3,3,3-tetrafluoropropene with substantially no 1,1,1,3,3-pentafluoropropene by allowing the reaction of the 1,1,1,3,3-pentafluoropropane and the base to proceed with a conversion rate of 99.99% as in the after-mentioned working examples.

The base used in the third step is a hydroxide of an alkali metal or a hydroxide of an alkaline earth metal. The alkali metal is lithium, sodium, potassium, rubidium or cesium. The alkaline earth metal is magnesium, calcium or strontium.

Specific examples of the alkali metal hydroxide and alkaline earth metal hydroxide are lithium hydroxide, sodium hydroxide, potassium hydroxide, calcium hydroxide, magnesium hydroxide and strontium hydroxide. Among others, potassium hydroxide, sodium hydroxide, calcium hydroxide and magnesium hydroxide are preferred. Particularly preferred are potassium hydroxide and sodium hydroxide, each of which is industrially available in a large quantity at a low cost.

These bases can be used solely or in combination of two or more kinds thereof in the third step.

It is necessary in the third step to use the base in an amount of at least 1 mol per 1 mol of the reaction mixture containing the cis-1,3,3,3-tetrafluoropropene and the 1,1,1,3,3-pentafluoropropane. In general, the amount of the base used can be adjusted as appropriate within the range of 1 to 10 mol and is preferably 1 to 4 mol, more preferably 1 to 2 mol. Although the base may be used in an amount exceeding 10 mol, there is no merit in using such a large amount of the base.

In the third step, the conversion rate of the reaction may be deteriorated when the amount of the base used is less than 1 mol per 1 mol of the reaction mixture containing the cis-1,3,3,3-tetrafluoropropene and the 1,1,1,3,3-pentafluoropropane.

As the above-mentioned base is solid at room temperature and atmospheric pressure, it is feasible to add at least one kind of solvent as required such that the reaction proceeds in a solution. The solvent can be selected as appropriate by those skilled in the art. There is no particular limitation on the kind of the solvent used as long as the reaction is not involved in the reaction. Specific examples of the solvent are: alkanes such as n-pentane, n-hexane, n-heptane and n-octane; aromatic hydrocarbons such as benzene, toluene and xylene; ethers such as diethyl ether, tetrahydrofuran and dioxane; halogenated hydrocarbons such as dichloromethane and chloroform; ketones such as acetone, methyl ethyl ketone and methyl isobutyl ketone; nitriles such as acetonitrile, propionitrile and butylnitrile; amides such as N,N-dimethylformamide (DMF), N,N-dimethylacetamide (DMAC) and hexamethylphosphoric triamide (HMPA); glycols such as ethylene glycol, diethylene glycol, ethylene glycol monomethyl ether and ethylene glycol monoacetate; alcohols such as methanol, ethanol and 2-propanol; and water. These solvents can be used solely or in combination of two or more kinds thereof.

For example, it is a particularly preferred embodiment of the present invention to use potassium hydroxide as the base and water as the solvent as in the after-mentioned working examples.

In addition to the solvent, a phase transfer catalyst may be used as an additive in the third step. The phase transfer catalyst is preferably used to promote the reaction in particular in the case where the alkali metal hydroxide is used as the base.

As the phase transfer catalyst, there can be used crown ether, cryptate or onium salt. The crown ether is able to increase the reactivity by encapsulation of a metal cation. Specific examples of such a combination of the crown ether and the metal cation are a combination of K cation and 18-crown-6, a combination of Na cation and 15-crown-5 and a combination of Li cation and 12-crown-4. A dibenzo or dicylcohexano derivative of the crown ether is also usable as the phase transfer catalyst.

The cryptand is a polycyclic macrocyclic chelating agent able to form a complex (cryptate) with e.g. K cation, Na cation, Rb cation, Cs cation or Li cation and activate the reaction. Specific example of the cryptate are 4,7,13,18-tetraoxa-1,10-diazabicyclo[8.5.5]icosane (cryptand 211) and 4,7,13,16,21,24-hexaoxa-1,10-diazabicyclo[8.8.8]hexacosane (cryptand 222).

The onium salt can be a quaternary ammonium salt or a quaternary phosphonium salt. Specific examples of the onium salt are tetramethylammonium chloride, tetramethylammonium bromide, tetra-n-butylammonium chloride, tetra-n-butylammonium bromide, benzyltriethylammonium chloride, methyltrioctylammonium chloride, tetra-n-butylphosphonium chloride, tetra-n-butylphosphonium bromide and methyltriphenylphosphonium chloride.

There occurs no generation of corrosive gas in the third step. There is thus no particular limitation on the material of the reactor as long as the material of the reactor is capable of withstanding the pressure conditions of the reaction, such as ordinary pressure or pressurized conditions. The reactor can be formed of ordinary stainless steel, glass or fluoro resin or can be formed of a material having a lining of glass or fluoro resin.

In the third step, the cis-1,3,3,3-tetrafluoropropene is obtained by flowing the reaction product gas into a cooled condenser and collecting and liquefying the product gas in a collection vessel. Although a slight amount of trans-1,3,3,3-tetrafluoropropene may be contained in the thus-obtained reaction product, it is feasible to yield the cis-1,3,3,3-tetrafluoropropene with a high purity by further distillation of the obtained cis-1,3,3,3-tetrafluoropropene product.

It is a particularly preferred embodiment of the present invention to purify the cis-1,3,3,3-tetrafluoropropene by distillation after the third step for production of the high-purity cis-1,3,3,3-tetrafloropropene. There is no particular limitation on the material of the distillation column used in the distillation. The distillation column may be formed of glass or stainless steel or may be formed with an inner lining of tetrafluoroethylene resin, chlorotrifluoroethylene resin, vinylidene fluoride resin, PFA resin or glass. Further, the distillation column may be packed with a packing material. It is preferable to perform the distillation at ordinary pressure or under pressurized conditions as in the case of the second step. There is no particular limitation on the number of stages of the distillation column required for the distillation. The number of stages of the distillation column is preferably 5 to 100, more preferably 10 to 50.

In this way, the present invention makes it possible to realize production of the high-purity cis-1,3,3,3-tetrafluoropropene by the above steps.

As the trans-1,3,3,3-tetrafluoropropene is formed simultaneously with cis-1,3,3,3-tetrafluoropropene and separated in the second step, the present invention also makes it possible to realize efficient simultaneous production of the cis and trans structural isomers of 1,3,3,3-tetrafluoropropene using industrially readily available 1,1,1,3,3-pentafluoropropane as the raw material.

It is feasible in the present invention to convert the separated trans-1,3,3,3-tetrafluoropropene to 1,1,1,3,3-pentafluoropropane and recycle the 1,1,1,3,3-pentafluoropropane as the raw material of the first step although the separated trans-1,3,3,3-tetrafluoropropene can be used for any other applications.

One example of the conditions of the conversion reaction is to react the trans-1,3,3,3-tetrafluoropropene with hydrogen fluoride in a gas phase in the presence of a catalyst. The hydrogen fluoride used in the conversion reaction may be the one separated by the second step or may be the new one prepared separately.

More specifically, the conversion reaction can be performed by reacting the trans-1,3,3,3-tetrafluoropropene with excessive hydrogen fluoride in a gas phase with the use of a solid catalyst that carries antimony pentachloride, antimony trichloride, antimony pentabromide, antimony tribromide, tin tetrachloride, titanium tetrachloride, molybdenum pentachloride, tantalum pentachloride, niobium pentachloride etc. on a carrier such as activated carbon, fluorinated alumina or fluorinated zirconia, or reacting the trans-1,3,3,3-tetrafluoropropene with hydrogen fluoride in a liquid phase with the use of antimony pentachloride, antimony trichloride, antimony pentabromide, antimony tribromide, tin tetrachloride, titanium tetrachloride, molybdenum pentachloride, tantalum pentachloride, niobium pentachloride etc. as the catalyst.

It is a particularly preferred embodiment of the present invention to continuously react the trans-1,3,3,3-tetrafluoropropane with hydrogen fluoride by the use of a catalyst that carries antimony pentachloride on activated carbon.

The 1,1,1,3,3-pentafluoropropane discharged out of the reactor and containing excessive hydrogen fluoride can be returned as it is to the reaction system of the first step.

EXAMPLES

The present invention will be described in more detail below by way of the following examples. It is herein noted that the unit "%" of respective organic composition analysis values means "area %" as directly measured by gas chromatography (using FID as a detector unless otherwise specified). Further, the term "cis-1234ze" refers to cis-1,3,3,3-tetrafluoropropene; the term "trans-1234ze" refers to trans-1,3,3,3-tetrafluoropropene; and the term "HFC-245fa" refers to 1,1,1,3,3-pentafluoropropane.

Preparation Example

Into methanol, 225 g of special grade $ZrOCl_2.8H_2O$ was dissolved. Then, 2.5 liter of spherical alumina of 5 mm diameter were immersed and left in the resulting solution for one day. The solvent was distilled out. The alumina was recovered and dried at 120° C. under the flow of nitrogen. The thus-obtained zirconium compound-carrying alumina was packed into a reaction tube. The reaction tube used herein was a cylindrical type reaction tube formed of SUS 316 with a diameter of 4.12 cm and a length of 270 cm and equipped with an electric furnace. While flowing nitrogen gas into the reaction tube, the temperature of the reaction tube was raised to 200° C. At the time water leak was no longer seen, hydrogen fluoride was fed together with the nitrogen gas into the reaction tube. The concentration of the hydrogen fluoride was gradually increased. The temperature of the reaction tube was raised to 450° C. at the time a hot spot caused by fluorination of the zirconium compound-carrying alumina reached the outlet of the reaction tube. In such a state, the zirconium compound-carrying alumina was kept heated for 1 hour. By this, the preparation of the catalyst was completed.

Example 1

First Step

Dehydrofluorination of 1,1,1,3,3-Pentafluoropropane and Second Step: Distillation Operation Provided was a gas-phase reaction system having a cylindrical reaction tube (SUS 316, diameter: 4.12 cm, length: 270 cm) capable of being heated by an external heating device. This reaction tube was packed with 1.7 liter of the catalyst prepared in the above preparation example. While flowing nitrogen gas into the reaction tube at a rate of about 6.81 l/min, the temperature of the reaction tube was raised to 330° C. Further, hydrogen fluoride was fed into the reaction tube at a rate of about 6.8 g/min for 1 hour. After that, the introduction of the nitrogen gas and hydrogen fluoride was stopped. As the organic raw material, 1,1,1,3,3-pentafluoropropane was gasified in advance and supplied into the reaction tube at a rate of about 61 g/min.

The product gas flowing out of the reaction tube was blown into water for removal of acidic gas. The resulting product gas was passed through a drying column packed with Molecular sieves 3A (trade name), and then, collected in a dry-ice/acetone trap. This reaction was continued for 12 hours. As a result, 37.58 kg of organic substance was collected as the reaction product. The collected organic substance was analyzed by gas chromatography. The analytical results showed that the composition of the reaction product was 66.47% trans-1234ze, 17.74% cis-1234ze and 15.70% HFC-245fa.

The reaction product was subjected to distillation. During the distillation, the trans-1234ze was separated as an initial distillate fraction; and the cis-1234ze was condensed and collected as a subsequent distillate fraction. The cis-1234ze distillate fraction was also analyzed by gas chromatography. The analytical results showed that the composition of the cis-1234ze distillate fraction was 10.86% HFC-245fa and 89.04% cis-1234ze.

Third Step

Reaction with Base and Distillation Operation after Third Step

To a 10-liter jacketed autoclave of SUS 316, a double-tube condenser of sus316 was attached. An aqueous ethylene glycol solution of −5° C. was circulated in a jacket of the condenser. The autoclave was vacuumed by a vacuum pump. An aqueous ethylene glycol solution of −5° C. was also circulated in a jacket of the autoclave. Subsequently, 57 g of tetra-n-butylammonium bromide, 2302 g of 48 wt % aqueous potassium hydroxide solution (potassium hydroxide content: 19.7 mol) and 8170 g (70.6 mol) of the cis-1234ze-containing organic fraction (HFC-245fa content: 10.86%, cis-1234ze content: 89.04%) were introduced into the autoclave. The resulting mixture was stirred with a stirrer and heated for 19 hours by circulating hot water of 40 to 45° C. in the jacket of the autoclave. After the completion of the reaction, the cooling of the condenser was stopped. Then, 7623 g of the reaction product was collected in a dry-ice/acetone cooled gas trap. It was confirmed that: the rate of conversion of the HFC-245fa was 99.99%; and the composition of the reaction product was 7.41% trans-1234ze and 92.35% cis-1234ze. When the reaction product was purified by distillation, 6480 g of the cis-1234ze was obtained with a purity of 99.9%.

INDUSTRIAL APPLICABILITY

The target compound of the present invention, i.e., cis-1,3,3-tetrafluoropropene is useful as an intermediate for production of pharmaceutical and agrichemical products and functional materials.

The invention claimed is:

1. A method for production of cis-1,3,3,3-tetrafluoropropene, comprising:
    a first step of subjecting 1,1,1,3,3-pentafluoropropane to dehydrofluorination to form a reaction mixture containing cis-1,3,3,3-tetrafluoropropene, trans-1,3,3,3-tetrafluoropropene and unreacted 1,1,1,3,3-pentafluoropropane;
    a second step of distilling the reaction mixture formed by the first step to separate the trans-1,3,3,3-tetrafluoropropene from the reaction mixture and collect a reaction mixture containing the cis-1,3,3,3-tetrafluoropropene and 1,1,1,3,3-pentafluoropropane; and
    a third step of reacting the reaction mixture collected by the second step and containing the cis-1,3,3,3-tetrafluoropropene and 1,1,1,3,3-pentafluoropropane with a base and thereby obtaining the cis-1,3,3,3-tetrafluoropropene from the reaction mixture.

2. The method according to claim 1, wherein, in the first step, the dehydrofluorination is performed in a gas phase in the presence of a catalyst.

3. The method according to claim 2, wherein the catalyst is a zirconium compound-carrying catalyst that carries a zirconium compound on a metal oxide or activated carbon.

4. The method according to claim 3, wherein the metal oxide is at least one kind selected from the group consisting of alumina, zirconia, titania and magnesia.

5. The method according to claim 3, wherein the zirconium compound is in the form of at least one kind selected from the group consisting of a nitrate, a phosphate, a fluoride, a chloride, a fluorochloride, an oxyfluoride, an oxychloride and an oxyfluorochloride.

6. The method according to claim 1, wherein the first step or the second step includes removing hydrogen fluoride from the reaction mixture.

7. The method according to claim 1, further comprising: a step of converting the trans-1,3,3,3-tetrafluoropropene separated by the distillation of the second step to 1,1,1,3,3-pentfluoropropane, and then, recycling the 1,1,1,3,3-pentfluoropropane as the raw material of the first step.

8. The method according to claim 7, wherein the conversion of the trans-1,3,3,3-tetrafluoropropene is performed by reaction with hydrogen fluoride in a gas phase in the presence of a catalyst.

9. The method according to claim 1, wherein the base used in the third step is a hydroxide of an alkali metal or a hydroxide of an alkaline earth metal.

10. The method according to claim 9, wherein the alkali metal is lithium, sodium, potassium, rubidium or cesium; and wherein the alkaline earth metal is magnesium, calcium or strontium.

11. A method for simultaneous production of cis-1,3,3,3-tetrafluoropropene and trans-1,3,3,3-tetrafluoropropene, comprising:
    a first step of subjecting 1,1,1,3,3-pentafluoropropane to dehydrofluorination to form a reaction mixture containing cis-1,3,3,3-tetrafluoropropene, trans-1,3,3,3-tetrafluoropropene and unreacted 1,1,1,3,3-pentafluoropropane;
    a second step of distilling the reaction mixture formed by the first step to separate the trans-1,3,3,3-tetrafluoropropene from the reaction mixture and collect a reaction mixture containing the cis-1,3,3,3-tetrafluoropropene and the 1,1,1,3,3-pentafluoropropane; and
    a third step of reacting the reaction mixture collected by the second step containing the cis-1,3,3,3-tetrafluoropropene and 1,1,1,3,3-pentafluoropropane with a base and thereby obtaining the cis-1,3,3,3-tetrafluoropropene from the reaction mixture.

\* \* \* \* \*